United States Patent [19]

Warriner

[11] Plant 4,460

[45] Sep. 18, 1979

[54] ROSE PLANT

[75] Inventor: William A. Warriner, Tustin, Calif.

[73] Assignee: Jackson & Perkins Company, Medford, Oreg.

[21] Appl. No.: 951,294

[22] Filed: Oct. 13, 1978

[51] Int. Cl.[2] ..... A01H 5/00

[52] U.S. Cl. ..... Plt./11

[58] Field of Search ..... Plt./11

*Primary Examiner*—Robert. E. Bagwill

*Assistant Examiner*—James R. Feyrer

*Attorney, Agent, or Firm*—Klarquist, Sparkman, Campbell, Leigh, Hall & Whinston

[57] ABSTRACT

A low growing, well branched rose plant of the hybrid tea class, having large foliage, long buds, and an open flower of 45 to 50 Rose Opal petals with a lighter reverse petal color and pronounced yellow base, having moderate fragrance.

6 Drawing Figures

BACKGROUND OF THE INVENTION

The present invention relates to a new and distinct variety of rose plant of the hybrid tea class which was originated by me by crossing two unnamed varieties of rose plants, one a yellow hybrid tea, the other a red hybrid tea.

The primary objective of this breeding was to produce a new rose variety of the hybrid tea class with blooms, borne freely, of a blend of soft colors, not a bicolor. The objective was substantially achieved along with other desirable traits as evidenced by the following unique combination of characteristics which are outstanding in the new variety and which distinguish it from its parents as well as from all other varieties of which I am aware:

1. A vigorous, upright, well branched plant of medium height, normally about four feet, sometimes reaching five feet when grown at Irvine, Calif.
2. Large leathery foliage, normally resistant to mildew, but sometimes showing infection by the disease.
3. A long bud with slightly blunt or flat terminal end which opens slowly.
4. Petalage of 45 to 50 petals.
5. Color of Claret Rose in the bud to a light Rose Opal in the full open form, the lower side of the petals being considerably lighter at all stages.
6. Petal base color of Sulphur Yellow, sharply defined on upper side of petals, blended into Rose Opal on lower side.
7. A moderately strong fragrance.

Asexual reproduction of this new cultivar by budding as performed at Wasco, Calif., shows that the foregoing characteristics and distinctions come true to form and are established and transmitted through succeeding propagations.

The accompanying illustration shows typical specimens of the vegetative growth and flowers of this new cultivar in different stages of development, depicted in color as nearly true as it is reasonably possible to make the same in a color illustration of this character.

The following is a detailed description of my new rose cultivar with color in terminology in accordance with Wilson's Horticultural Color Chart, except where ordinary dictionary significance of color is indicated.

Parentage:

*Seed parent.*—Unnamed variety.

*Pollen parent.*—Unnamed variety.

Classification:

*Botanical.*—Rosa hybrid.

*Commercial.*—Hybrid tea.

FLOWER

Observations made from specimens grown at Irvine, Calif., in July of 1978.

Blooming habit: Continuous

Bud:

*Size.*—1 to 1¼ inches when petals start to unfurl.

*Form.*—Long, blunt top.

*Color.*—When sepals first divide, near Claret Rose (021); when half blown, upper side of petals ranging from Claret Rose (021) to Claret Rose (021/1); lower side of petals, from Claret Rose (021/2) to Claret Rose (021/3) to near white.

*Sepals.*—Color: Outer surface Scheele's Green (860/2) overlaid often with Garnet Brown (00918/3); inner surface, Scheele's Green (860/3) with a light tomentum. Three appendaged sepals, lightly appendaged. Two unappendaged sepals, hairy edged.

*Receptacle.*—Color: Scheele's Green (860/2), sometimes overlaid with Garnet Brown (00918/3). Shape: funnel. Size: large, broad. Surface: smooth and glaucescent.

*Peduncle.*—Length: short. Surface: smooth, occasionally with a few stipitate glands. Color: bronzy. Strength: stiff, erect, heavy.

*Opening.*—Outer petals curl back.

Bloom:

*Size.*—Large. Average open size 5 inches.

*Borne.*—Mostly singly.

*Stems.*—Medium and strong.

*Form.*—When first open, high centered. Permanence — retains its form to the end.

*Petalage.*—Number of petals under normal conditions: 45—50.

*Color.*—Center of flower: Upper side of petals — near Rose Opal (022); reverse side of petals — Rose Opal (022/3). Base of petals: upper side — sharply defined area (approximately ⅜" long) of SulphurYellow (1/1); lower side — larger area, not sharply defined of Sulphur Yellow (1/3). General tonality from a distance: bicolor effect when half open of Rose Opal (022) and Rose Opal (022/3) with much light Sulphur Yellow (1/3) evident from base of petals, lower side.

*Variegation.*—Occasionally a whitish midrib.

*Discoloration.*—Color tends to lighten after several days to Rose Opal (022/3) overall.

*Fragrance.*—Moderate.

Petals:

*Texture.*—Thick.

*Shape.*—Round.

*Form.*—Tips slightly recurved.

*Arrangement.*—Imbricated. Petaloids in center, few.

*Persistence.*—Hang on and dry.

*Lastingness.*—On the plant, long. As cut flower, long.

Reproductive parts:

*Anthers.*—Medium. Color, yellow. Arrangement, regular around styles.

*Filaments.*—Color: yellow.

*Pollen.*—Gold yellow.

*Styles.*—Color: reddish.

*Stigmas.*—Color: white.

PLANT

Form: Bush.

Growth: Very vigorous, upright, branching, compact.

Foliage: Number of leaflets on normal mid-stem leaves 5–7.

Size: Large.

Quantity: Normal.

Color: New foliage: Garnet Brown (00918). Old foliage: Spinach Green (0960).

Leaflets:

*Shape.*—Elliptic.

*Texture.*—Upper side: leathery, slightly corrugated.

*Edge.*—Serrated.

*Serrations.*—Single, small.

*Petiole.*—Rachis: Color, reddish. Underside, prickles.

*Stipules.*—Long, bearded.

*Disease resistance.*—Normally resistant to mildew under normal growing conditions at Irvine, Calif.

Wood:

*New wood.*—Color: bronzy brown. Bark: smooth.

*Old wood.*—Color: green to brown. Bark: smooth.

Prickles:

*Quantity.*—On main stalks from base, ordinary. On laterals from stalk, ordinary.

*Form.*—Long base, hooked downward.

*Color when young.*—Brown.

*Position.*—Irregular.

Small prickles:

*Quantity.*—On main stalks, none. On laterals, none.

I claim:

1. A new and distinct variety of rose plant of the hybrid tea class, substantially as herein shown and described, characterized particularly as to novelty by the unique combination of its low growing, well branched plant, large foliage, long bud, open flower of 45 to 50 Rose Opal petals with a lighter reverse and pronounced yellow base and moderate fragrance.

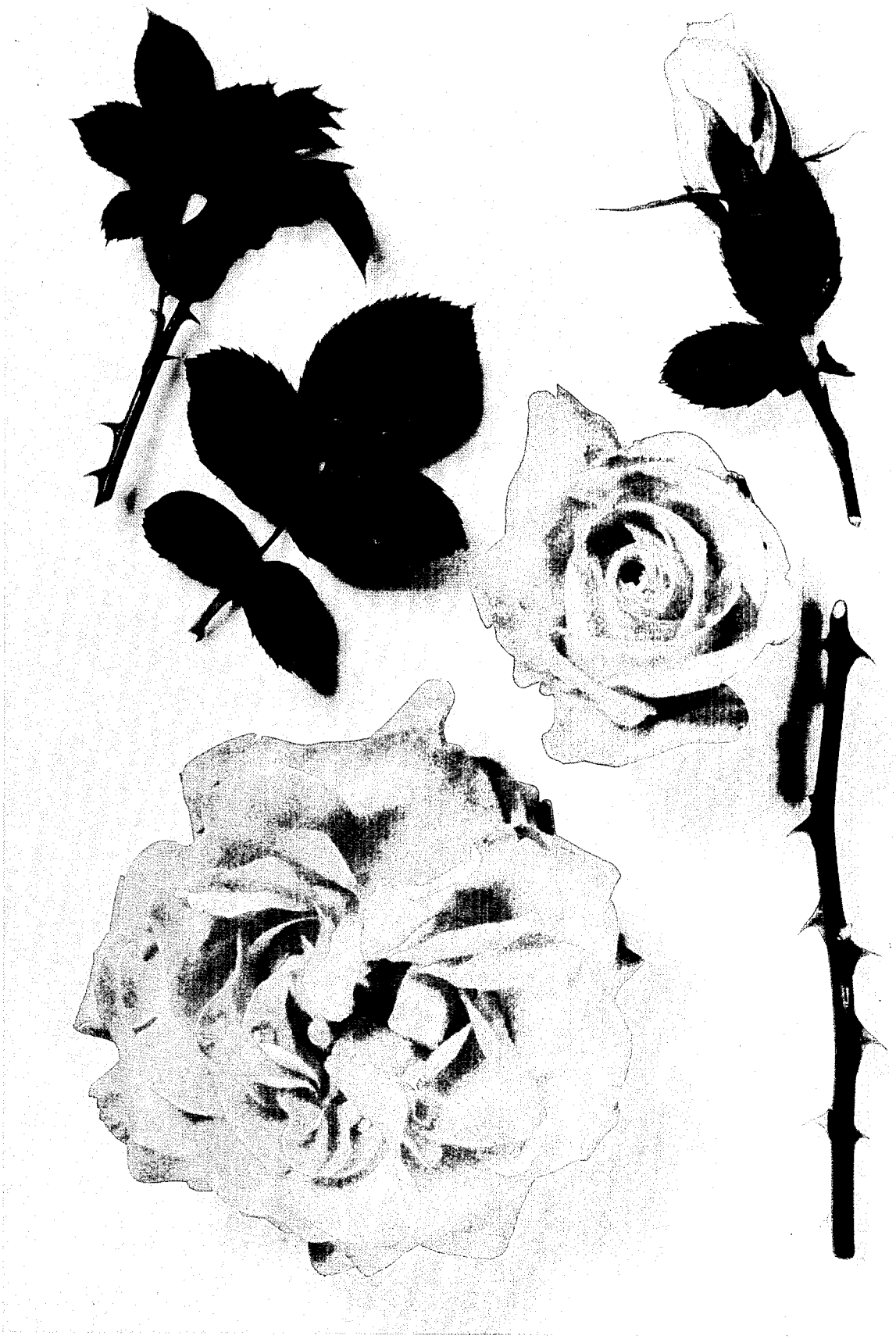

* * * * *